United States Patent
Suzuki et al.

(10) Patent No.: US 10,307,039 B2
(45) Date of Patent: Jun. 4, 2019

(54) ENDOSCOPE

(71) Applicant: FUJIFILM Corporation, Tokyo (JP)

(72) Inventors: Issei Suzuki, Kanagawa (JP); Takashi Yashiro, Kanagawa (JP); Shuichi Ishii, Kanagawa (JP); Kazuaki Takahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 186 days.

(21) Appl. No.: 15/203,816

(22) Filed: Jul. 7, 2016

(65) Prior Publication Data

US 2017/0007096 A1 Jan. 12, 2017

(30) Foreign Application Priority Data

Jul. 10, 2015 (JP) ................................. 2015-138945
Feb. 15, 2016 (JP) ................................. 2016-025950

(51) Int. Cl.
*A61B 1/00* (2006.01)
*A61B 18/18* (2006.01)
*A61B 1/05* (2006.01)
*A61B 18/00* (2006.01)

(52) U.S. Cl.
CPC .......... *A61B 1/0008* (2013.01); *A61B 1/0011* (2013.01); *A61B 1/051* (2013.01); *A61B 18/18* (2013.01); *A61B 1/00114* (2013.01); *A61B 2018/00982* (2013.01)

(58) Field of Classification Search
CPC . A61B 1/0008; A61B 1/0011; A61B 1/00114; A61B 1/051; A61B 18/18; A61B 2018/00982; A61B 1/05
See application file for complete search history.

(56) References Cited

U.S. PATENT DOCUMENTS 5,543,831 A * 8/1996 Tsuji ................... A61B 1/0669
128/901
2011/0245600 A1 10/2011 Ishii et al.

FOREIGN PATENT DOCUMENTS

JP 2011212161 10/2011

OTHER PUBLICATIONS

"Office Action of China Counterpart Application," dated Mar. 21, 2019, with English translation thereof, pp. 1-13.

* cited by examiner

*Primary Examiner* — Aaron B Fairchild
(74) *Attorney, Agent, or Firm* — JCIPRNET

(57) ABSTRACT

An endoscope includes in a tip portion of an insertion unit: an image sensor having plural terminals including a video terminal which outputs a video signal; and a tip potion of a treatment tool channel which extends in a longitudinal direction of the insertion unit, and a distance of the video terminal is longest among distances of the respective terminals from a center of the treatment tool channel in a plane that is perpendicular to the longitudinal axis.

4 Claims, 10 Drawing Sheets

ENDOSCOPE

CROSS-REFERENCE TO RELATED APPLICATIONS

This application claims the benefit of Japanese Patent Application JP 2015-138945, filed Jul. 10, 2015, and Japanese Patent Application JP 2016-025950, filed Feb. 15, 2016, the entire contents of which are hereby incorporated by reference, the same as if set forth at length.

FIELD OF THE INVENTION

The present invention relates to an endoscope that is equipped with an image sensor in a tip portion of an insertion unit to be inserted into a subject body.

BACKGROUND OF THE INVENTION

The insertion unit of an endoscope is equipped with a treatment tool channel through which a treatment tool is to be inserted. Not only is an observation part observed using an image sensor that is installed in a tip portion of the insertion portion, but also the observation part may be treated using a treatment tool that is inserted through the treatment tool channel.

An example treatment tool is a radio-frequency treatment tool such as an electric scalpel. JP-A-2011-212161 discloses an endoscope in which a shield piece is disposed so as to be continuous with a circuit board to which an image sensor is connected and exposed conductor portions of cables that are connected to the circuit board are covered with the shield piece. This measure suppresses mixing, into input and output signals of the image sensor, of noise that is radiated from a radio-frequency treatment tool.

SUMMARY OF THE INVENTION

Many things such as the image sensor, the treatment tool channel, and a light guide for guiding illumination light for illumination of an observation part are provided in the tip portion of the insertion unit.

Narrowing of insertion units of endoscopes is now demanded. To satisfy this demand, the image sensor and the treatment tool channel which occupy relatively large spaces among various things provided in the tip portion of the insertion unit are necessarily disposed very close to each other. As a result, input and output signals of the image sensor are prone to be affected by noise that is radiated from a radio-frequency treatment tool. If noise is mixed into a video signal that is output from the image sensor, it may obstruct execution of proper observation and treatment.

The present invention has been made in the above circumstances, and an object of the invention is therefore to provide an endoscope capable of reducing the influence of radio-frequency radiation that leaks from the treatment tool channel on a video signal of the image sensor without obstructing narrowing of the insertion unit.

An endoscope according to an aspect of the invention comprises in a tip portion of an insertion unit: an image sensor having plural terminals including a video terminal which outputs a video signal; and a tip potion of a treatment tool channel which extends in a longitudinal direction of the insertion unit, wherein: a distance of the video terminal is the longest among distances of the respective terminals from a center of the treatment tool channel in a plane that is perpendicular to the longitudinal axis.

The invention makes it possible to increase the resistance to noise that is radiated from a radio-frequency treatment tool inserted in the treatment tool channel without obstructing narrowing of the insertion unit.

DESCRIPTION OF SYMBOLS

Figure 1:
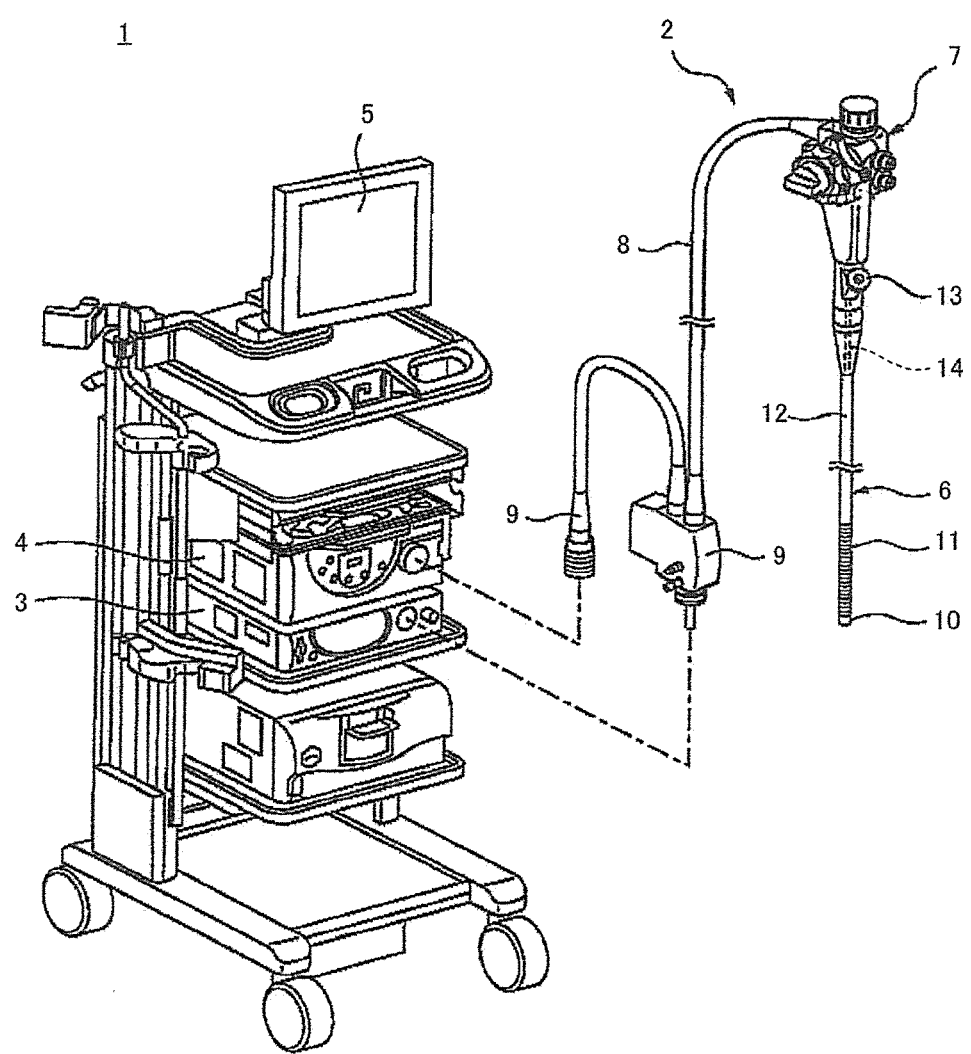
FIG. 1 shows the configuration of an endoscope system according to an embodiment of the present invention.

1: Endoscope system
2: Endoscope
3: Light source unit
4: Processor unit
5: Monitor
6: Insertion unit
7: Manipulation unit
8: Universal cord
9: Connectors
10: Tip portion
11: Bendable portion
12: Soft portion
13: Insertion inlet
14: Treatment tool channel
20: Image sensor
20a: Photodetecting surface
20b: Back surface
21: Objective optical system
21a: Objective optical element
22: Outlet
23: Terminals
23a: Video terminal
23b: Control terminal
23c: Power terminal
23d: Ground terminal
24: Cables
25: Flexible circuit board
26: Prism
27: Reflection surface
A: Longitudinal axis
C: Center La: Distance
Lb: Distance
Lc: Distance
Ld: Distance
S: Plane
S1: Plane
S2: Plane

DETAILED DESCRIPTION OF THE INVENTION

FIG. 1 shows an endoscope system 1 according to an embodiment of the present invention.

The endoscope system 1 is composed of an endoscope 2, alight source unit 3, and a processor unit 4. The endoscope 2 is equipped with an insertion unit 6 to be inserted into a subject body, a manipulation unit 7 which is continuous with the insertion unit 6, and a universal cord 8 which extends from the manipulation unit 7. The insertion unit 6 is composed of a tip portion 10, a bendable portion 11 which is continuous with the tip portion 10, and a soft portion 12 which links the bendable portion 11 to the manipulation unit 7.

The tip portion 10 is equipped with an illumination optical system for emitting illumination light for illumination of an observation part and an image sensor and an imaging optical system for shooting the observation part. The bendable portion 11 is configured so as to be bendable perpendicularly to the longitudinal axis of the insertion unit 6, and is bent by manipulating the manipulation unit 7. The soft portion 12 is configured so as to be flexible enough to deform so as to conform to the shape of an insertion route of the insertion unit 6.

The manipulation unit 7 is equipped with buttons for manipulating an imaging operation of the image sensor installed in the tip portion 10 and a rotary knob for making a manipulation for bending the bendable portion 11. The manipulation unit 7 is formed with an insertion inlet 13 through which a treatment tool such as an electric scalpel is to be inserted, and a treatment tool channel 14 through which a treatment tool is to be inserted is formed in the insertion unit 6 so as to extend from the insertion inlet 13 to the tip portion 10.

Connector 9 is provided at an intermediate position and one end of the universal cord 8. The endoscope 2 is connected, via the connector(s) 9, to the light source unit 3 for generating illumination light to be emitted from the illumination optical system provided in the tip portion 10 and the processor unit 4 for processing a video signal acquired by the image sensor provided in the tip portion 10. The processor unit 4 generates video data of an observation part by processing a received video signal and displays the generated video data on a monitor 5 and has it recorded.

A light guide and cables are disposed inside the insertion unit 6, the manipulation unit 7, and the universal cord 8. Illumination light generated by the light source unit 3 is guided by the light guide to the illumination optical system provided in the tip portion 10, and signals and power are transmitted between the image sensor provided in the tip portion 10 and the processor unit 4 by the cables.

Figure 2:
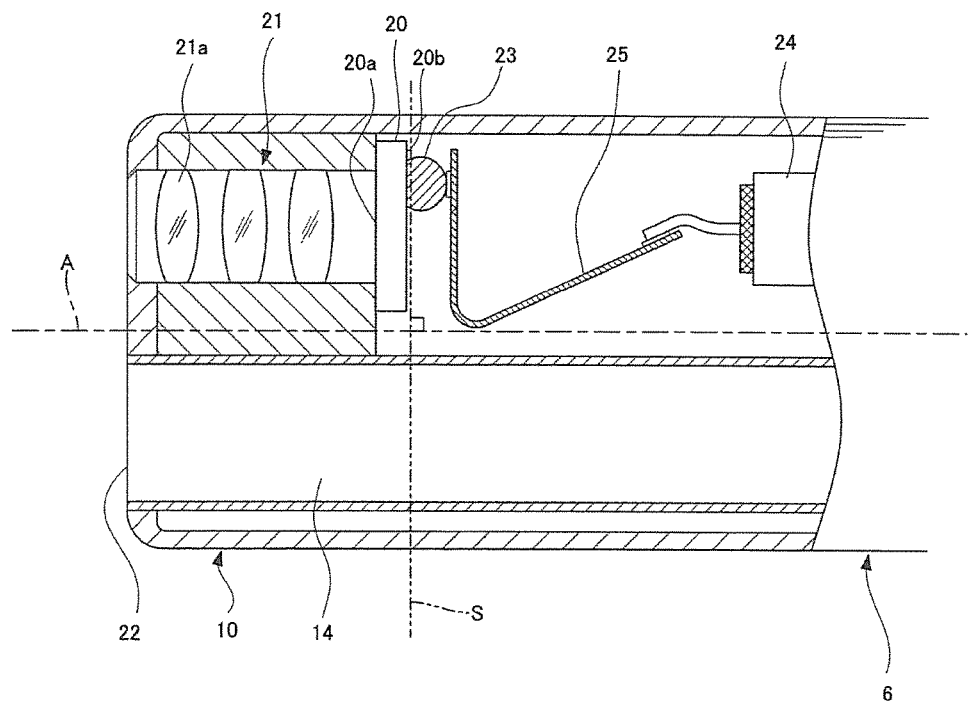
FIG. 2 is a sectional view of an example tip portion of an insertion unit of an endoscope shown in FIG. 1.

FIG. 2 shows the configuration of an example tip portion 10 of the insertion unit 6.

The tip portion 10 is equipped with an image sensor 20 such as a CCD (charge-coupled device) image sensor or a CMOS (complementary metal-oxide-semiconductor) image sensor, an objective optical system 21 for forming a subject image on a photodetecting surface 20a of the image sensor 20, and an outlet 22 of the treatment tool channel 14. Although not shown in FIG. 2, the illumination optical system for emitting illumination light that is guided from the light source unit 3 by the light guide and other members are disposed in the tip portion 10.

The photodetecting surface 20a of the image sensor 20 is disposed approximately perpendicularly to the longitudinal axis A of the insertion unit 6. The optical axis of the objective optical system 21 is approximately parallel with the longitudinal axis A of the insertion unit 6, and an objective optical element 21a that is disposed closest to the subject side among the optical elements constituting the objective optical system 21 is exposed in the end surface of the tip portion 10.

The treatment tool channel 14 extends approximately parallel with the longitudinal axis A of the insertion unit 6 and is disposed beside the image sensor 20 and the objective optical system 21, and the outlet 22 of the treatment tool channel 14 is opened in the end surface of the tip portion 10.

The image sensor 20 has plural terminals 23 including a video terminal for output of a video signal. In the illustrated example, the terminals 23 are provided on a back surface 20b, opposite to its photodetecting surface 20a, of the image sensor 20. The location where the terminals 23 are formed is not limited to the back surface 20b; they may be formed on a side surface of the image sensor 20.

The ends of the individual conductors of the cables 24 which connect the image sensor 20 to the processor unit 4 (see FIG. 1) are connected to the terminals 23 via a flexible circuit board 25. Example methods of connection between the flexible circuit board 25 and the terminals 23 are ACF (anisotropic conductive film) connection, NCF (non-conductive film) connection, and bump connection. The ends of the individual conductors of the cables 24 may be connected directly to the terminals 23.

Figure 3:
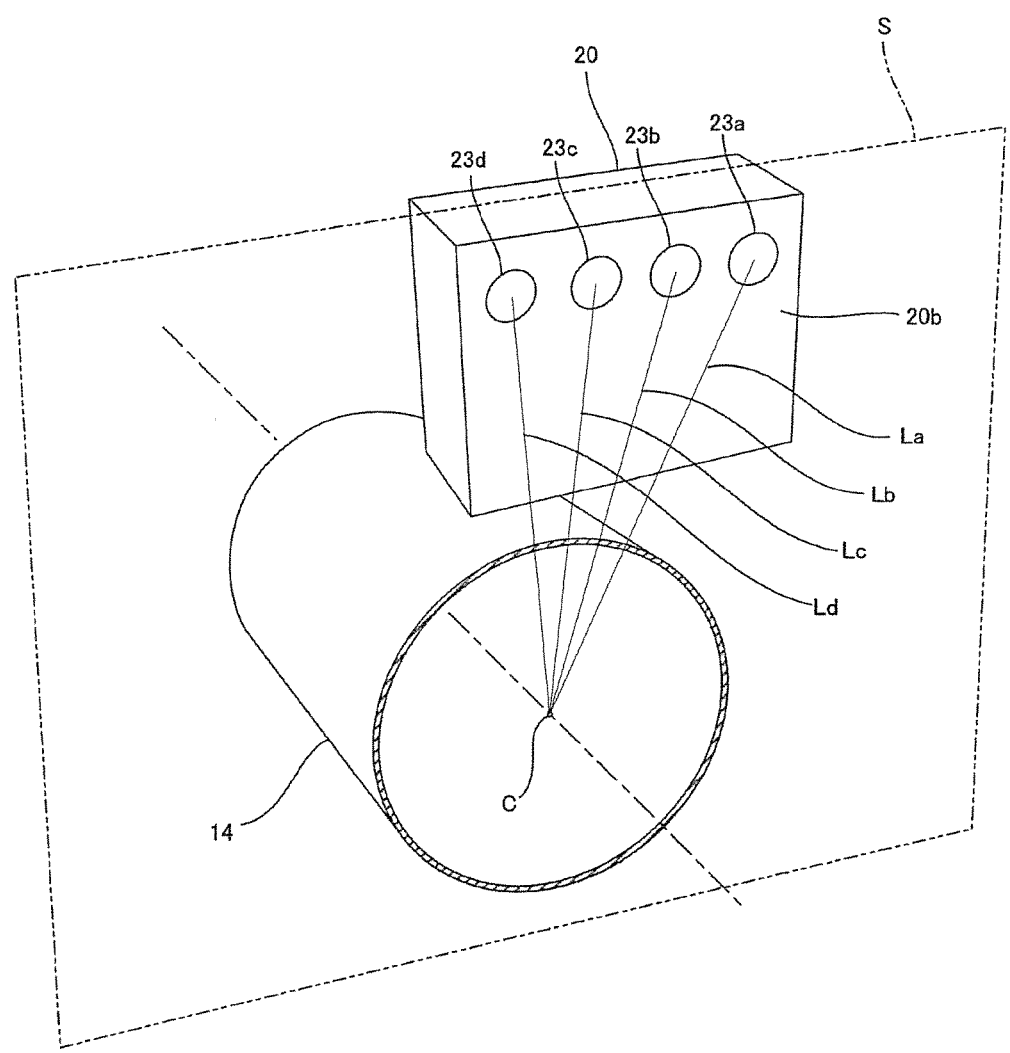
FIG. 3 is a schematic diagram showing an example layout of image sensor terminals in the tip portion of the insertion unit shown in FIG. 2.

FIG. 3 shows an example layout of the terminals 23 of the image sensor 20 in the tip portion 10 of the insertion unit 6 (see FIG. 2).

In the example shown in FIG. 3, the terminals 23 are four terminals, that is, a video terminal 23a for outputting a video signal, a control terminal 23b for receiving a control signal for controlling the operation of the image sensor 20, a power terminal 23c for receiving operation power for the image sensor 20, and a ground terminal 23d, which are arranged parallel with one, extending approximately perpendicularly to the arrangement direction of the image sensor 20/objective optical system 21 and the treatment tool channel 14, of the four sides of the approximately rectangular back surface 20b of the image sensor 20.

The video terminal 23a is most distant from the treatment tool channel 14. That is, the distance La of the video terminal 23a is the longest among the distances La-Ld of the respective terminals 23a-23d from the center C of the treatment tool channel 14 defined in a plane that is perpendicular to the longitudinal axis A of the insertion unit 6. In the illustrated example, since the video terminal 23a, the control terminal 23b, the power terminal 23c, and the ground terminal 23d are formed on the back surface 20b of the image sensor 20 which is disposed approximately perpendicularly to the longitudinal axis A, the distances La-Ld of the four terminals 23a-23d from the center C of the treatment tool channel 14 are defined in a common plane S that is perpendicular to the longitudinal axis A.

By disposing the video terminal 23a at a position that is most distant from the treatment tool channel 14, a phenomenon that noise that is radiated from a radio-frequency treatment tool inserted in the treatment tool channel 14 is mixed into a video signal that is output from the video terminal 23a can be suppressed, whereby a clear image that is necessary for proper observation and treatment can be obtained. The fact that the noise resistance of the endoscope 2 can be increased by the manner of disposition of the video terminal 23a rather than shielding contributes to narrowing of the insertion unit 6.

During observation and treatment, influence of noise tends to manifest itself in a video signal that is output from the video terminal 23a and is relatively prone to appear in a control signal that is input to the control terminal 23b. On the other hand, influence of noise is not prone to appear in operation power that is input to the power terminal 23c or on the ground.

It is preferable that as in the illustrated example the ground terminal 23d be disposed at a position that is closest to the treatment tool channel 14, that is, the distance Ld from the center C of the treatment tool channel 19 to the ground terminal 23d in the plane S be set shortest, or that the power terminal 23c be disposed at a position that is closest to the treatment tool channel 14, that is, the distance Lc from the center C of the treatment tool channel 14 to the power terminal 23c in the plane S be set shortest. With this measure, the noise resistance of the endoscope 2 can be increased further.

Figure 4:
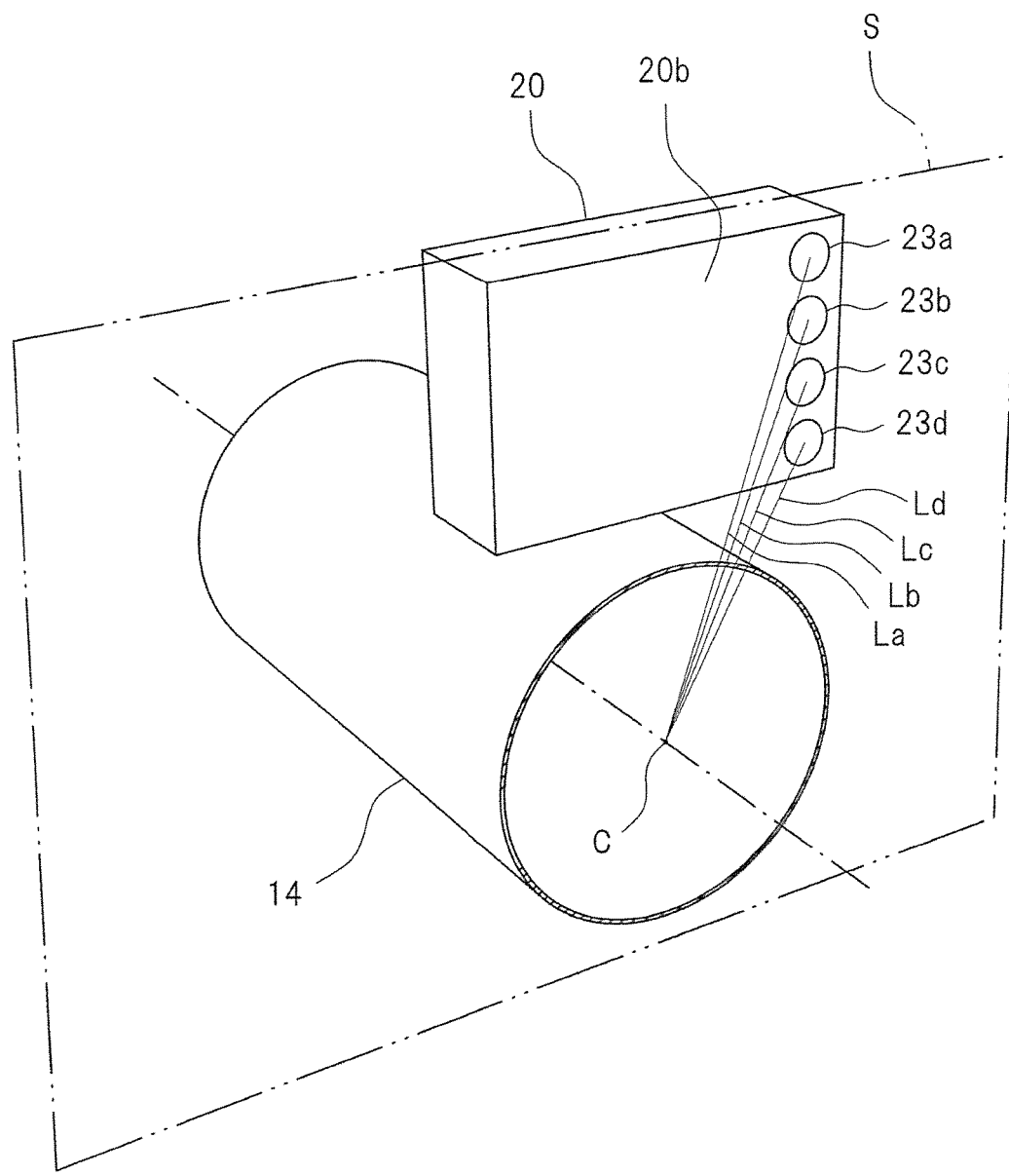
FIG. 4 is a schematic diagram showing another example layout of the image sensor terminals in the tip portion of the insertion unit shown in FIG. 2.

FIG. 4 shows another example layout of the terminals 23 of the image sensor 20 in the tip portion 10 of the insertion unit 6 (see FIG. 2).

In the example shown in FIG. 4, the terminals 23 are four terminals, that is, a video terminal 23a for outputting a video signal, a control terminal 23b for receiving a control signal for controlling the operation of the image sensor 20, a power terminal 23c for receiving operation power for the image sensor 20, and a ground terminal 23d, which are arranged parallel with one, extending in the arrangement direction of the image sensor 20/objective optical system 21 and the treatment tool channel 14, of the four sides of the approximately rectangular back surface 20b of the image sensor 20.

The video terminal 23a is most distant from the treatment tool channel 14. That is, the distance La of the video terminal 23a is the longest among the distances La-Ld of the respective terminals 23a-23d from the center C of the treatment tool channel 14 defined in a plane that is perpendicular to the longitudinal axis A of the insertion unit 6. The distances La-Ld of the four terminals 23a-23d from the center C of the treatment tool channel 14 are defined in a common plane S that is perpendicular to the longitudinal axis A.

As in the example shown in FIG. 3, by disposing the video terminal 23a at a position that is most distant from the treatment tool channel 14, a phenomenon that noise that is radiated from a radio-frequency treatment tool inserted in the treatment tool channel 14 is mixed into a video signal that is output from the video terminal 23a can be suppressed, whereby a clear image that is necessary for proper observation and treatment can be obtained. The fact that the noise resistance of the endoscope 2 can be increased by the manner of disposition of the video terminal 23a rather than shielding contributes to narrowing of the insertion unit 6.

The noise resistance of the endoscope 2 can be increased further by setting shortest the distance Ld from the center C of the treatment tool channel 14 to the ground terminal 23d in the plane S or disposing the power terminal 23c at a position that is closest to the treatment tool channel 14.

Figure 5:
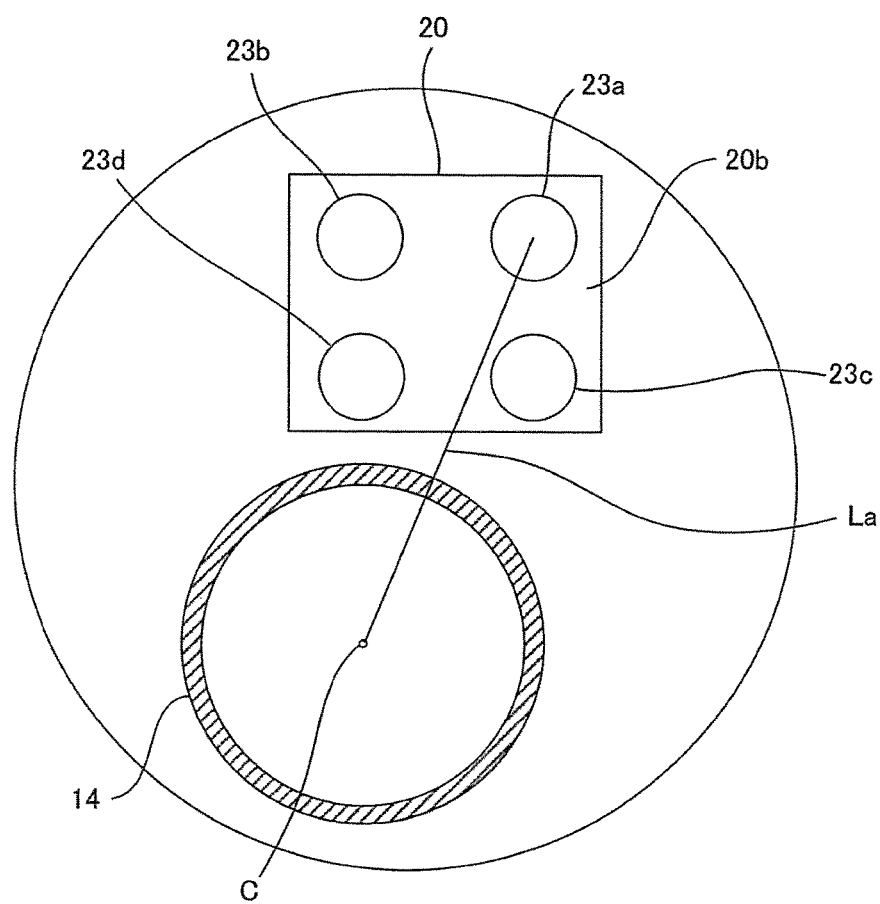
FIG. 5 is a schematic diagram showing still another example layout of the image sensor terminals in the tip portion of the insertion unit shown in FIG. 2.

FIG. 5 shows still another example layout of the terminals 23 of the image sensor 20 in the tip portion 10 of the insertion unit 6 (see FIG. 2).

In the example shown in FIG. 5, a video terminal 23a, a control terminal 23b, a power terminal 23c, and a ground terminal 23d are arranged in a matrix of two rows and two columns each of which is parallel with the corresponding one of the four sides of the back surface 20b of the image sensor 20. In this arrangement, the size of each of the terminals 23a-23d can be made larger than in the respective arrangements shown in FIGS. 3 and 4 in which the terminals 23a-23d are arranged parallel with one side of the back surface 20b. As a result, each of the terminals 23a-23d can be connected to a land of the flexible circuit board 25 or the conductor of a cable 24 easily and securely.

Also in the example of FIG. 5, the video terminal 23a is most distant from the treatment tool channel 14. That is, the distance La of the video terminal 23a is the longest among the distances of the respective terminals 23a-23d from the center C of the treatment tool channel 14 defined in a plane that is perpendicular to the longitudinal axis A of the insertion unit 6. As a result, the resistance to noise that is radiated from a radio-frequency treatment tool inserted in the treatment tool channel 14 can be strengthened without obstructing narrowing of the insertion unit 6.

Each of the above examples is such that the image sensor 20 is equipped with the four terminals, that is, the video terminal 23a, the control terminal 23b, the power terminal 23c, and the ground terminal 23d. However, the number of terminals 23 is not limited to four.

Figure 6:
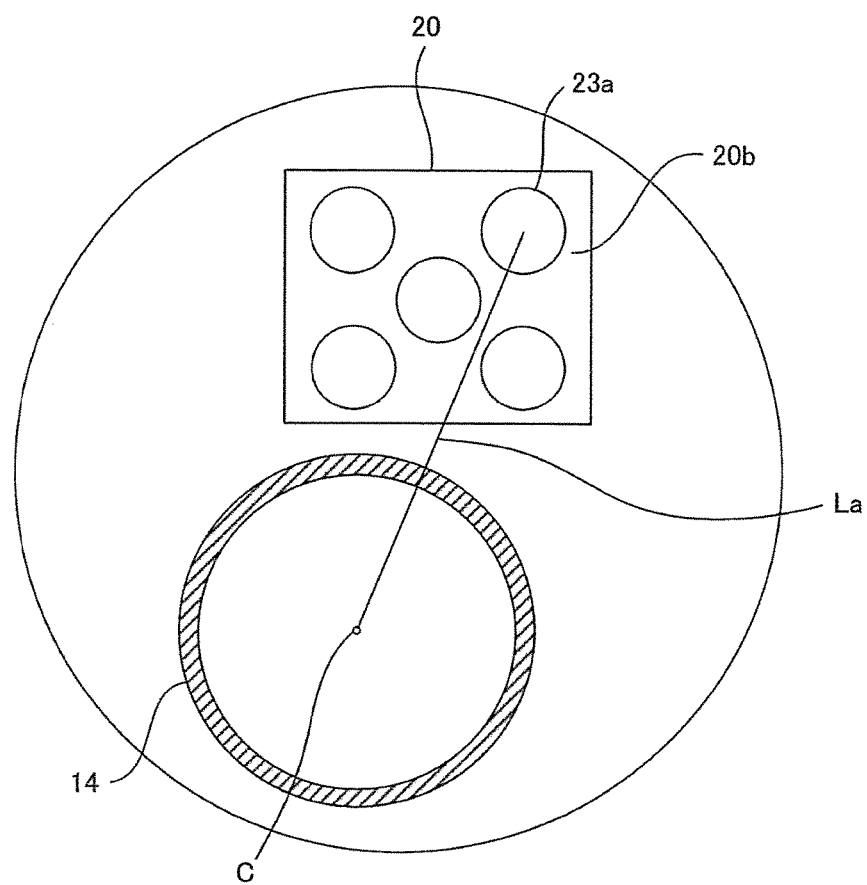
FIG. 6 is a schematic diagram showing yet another example layout of the image sensor terminals in the tip portion of the insertion unit shown in FIG. 2.

FIG. 6 shows an example in which a total of five terminals are formed; that is, a fifth terminal is formed in addition to a video terminal 23a, a control terminal 23b, a power terminal 23c, and a ground terminal 23d. Examples of the fifth terminal are an external clock terminal for receiving an external clock signal and a reset terminal for receiving a reset signal. Although no drawing is provided, a total of six terminals may be formed by adding both of an external clock terminal and a reset terminal.

Figure 7:
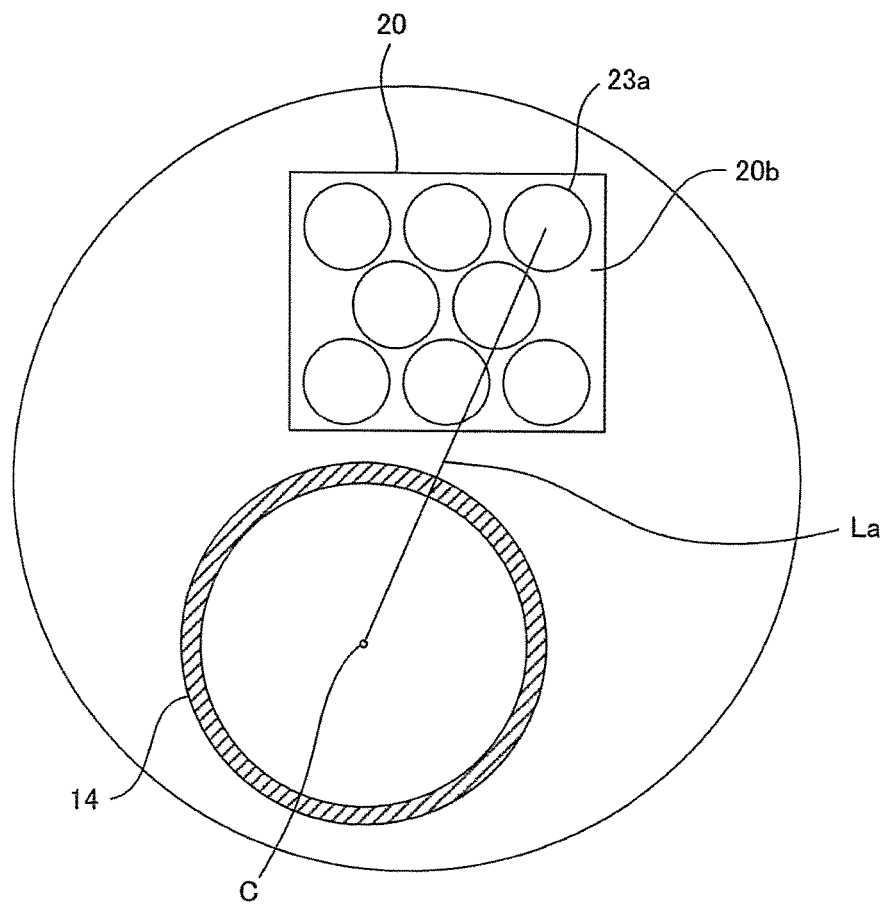
FIG. 7 is a schematic diagram showing a further example layout of the image sensor terminals in the tip portion of the insertion unit shown in FIG. 2.

FIG. 7 shows an example in which a control terminal 23b is divided into an SCS (serial chip select) terminal for receiving a chip select signal, an SCK (serial clock) terminal for receiving a serial clock signal, and an SI (serial data input) terminal for receiving serial data. Thus, a total of eight terminals are formed which are the three divisional control terminals, a video terminal 23a, a power terminal 23c, a ground terminal 23d, an external clock terminal, and a reset terminal.

In each of the examples shown in FIGS. 6 and 7, the video terminal 23a is formed at a position that is most distant from the treatment tool channel 14. That is, the distance La of the video terminal 23a is the longest among the distances of the respective terminals from the center C of the treatment tool channel 14 defined in a plane that is perpendicular to the longitudinal axis A of the insertion unit 6. As a result, the resistance to noise that is radiated from a radio-frequency treatment tool inserted in the treatment tool channel 14 can be strengthened without obstructing narrowing of the insertion unit 6.

A video signal can be transmitted being superimposed on any of various signals such as a control signal, an external clock signal, and a reset signal, in which case a total of three terminals are formed which are a signal terminal for input or output of a superimposition signal including a video signal, a power terminal, and a ground terminal. In this case, the signal terminal for input or output of a superimposition signal including a video signal is formed at a position that is most distant from the treatment tool channel 14.

Figure 8:
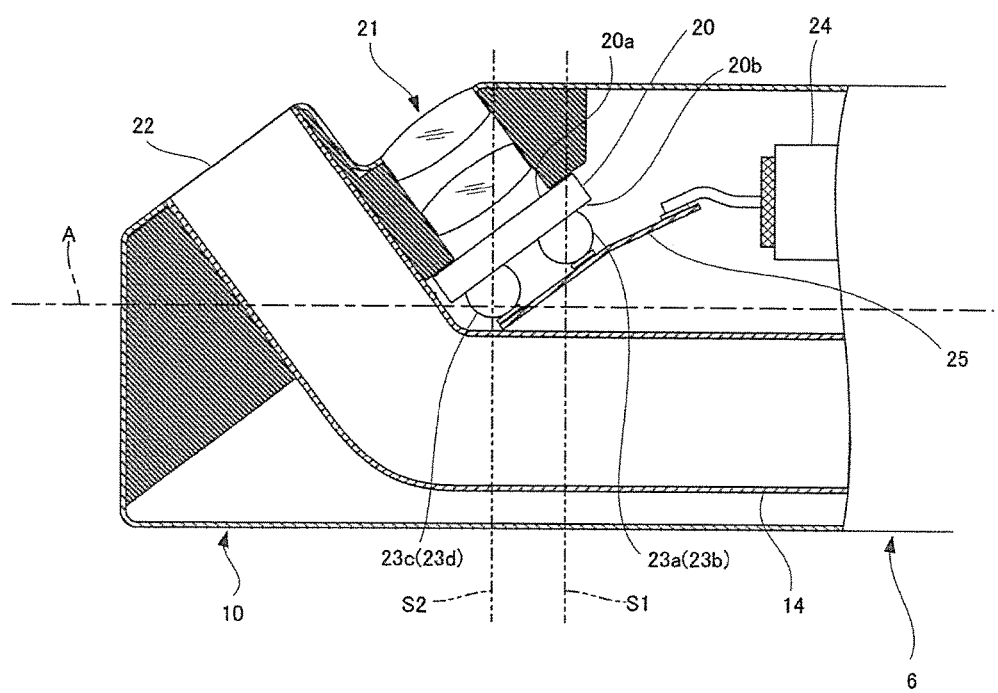
FIG. 8 is a sectional view of another example tip portion of an insertion unit of the endoscope shown in FIG. 1.

As shown in FIG. 8, the image sensor 20 may be disposed in such a manner that the photodetecting surface 20a and the back surface 20b opposite to it are oblique to the longitudinal axis A of the insertion unit 6. In this case, the distances of terminals 23a-23d from the centers of the treatment tool channel 14 are defined in different planes that are perpendicular to the longitudinal axis A.

In the example of FIG. 8, the video terminal 23a and the control terminal 23b are arranged on the back surface 20b parallel with its top side that is opposite to the treatment tool channel 14 and the power terminal 23c and the ground terminal 23d are arranged on the back surface 20b parallel with its bottom side that is adjacent to the treatment tool channel 14. The distances La and Lb of the video terminal 23a and the control terminal 23b are defined in a plane S1 that includes the video terminal 23a and the control terminal 23b and is perpendicular to the longitudinal axis A, and the distances Lc and Ld of the power terminal 23c and the ground terminal 23d are defined in a plane S2 that includes the power terminal 23c and the ground terminal 23d and is perpendicular to the longitudinal axis A.

Figure 9:
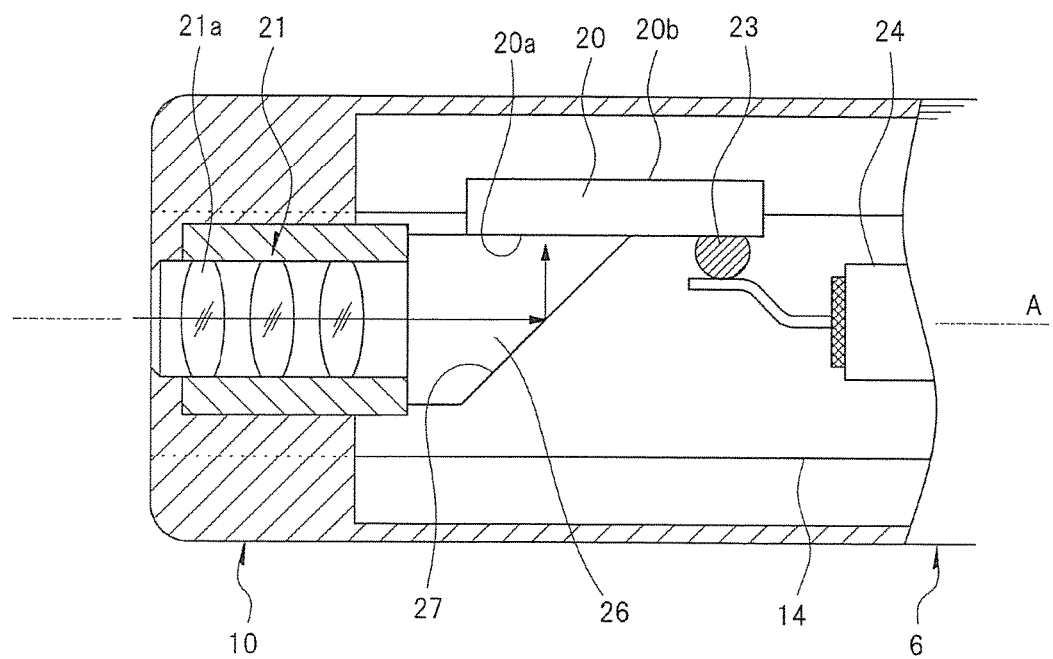
FIG. 9 is a sectional view of a further example tip portion of an insertion unit of the endoscope shown in FIG. 1.
Figure 10:
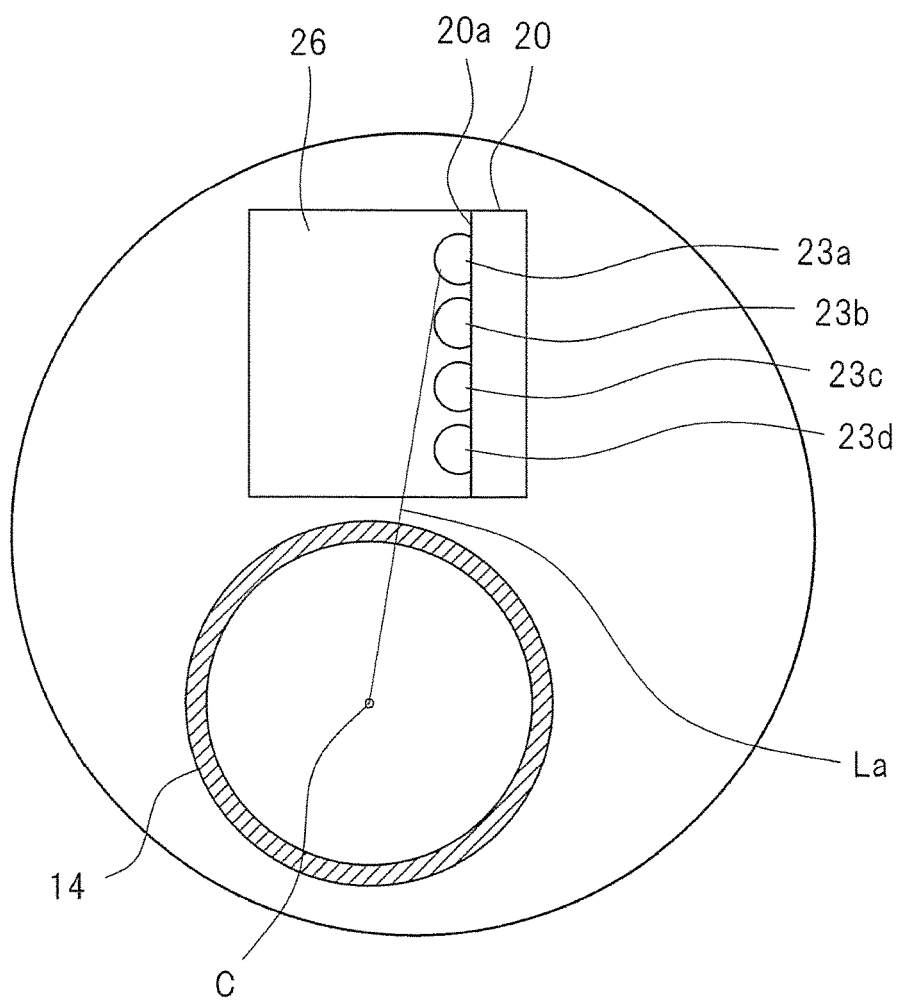
FIG. 10 is a schematic diagram showing an example layout of image sensor terminals in the tip portion of the insertion unit shown in FIG. 9.

FIG. 9 shows the configuration of a further example tip portion 10 of the insertion unit 6. FIG. 10 shows an example layout of the terminals 23 of the image sensor 20 in the tip portion 10 of the insertion unit 6 shown in FIG. 9.

In the example of FIGS. 9 and 10, the image sensor 20 is disposed in such a manner that its photodetecting surface 20a is approximately parallel with the longitudinal axis A of the insertion unit 6 and approximately perpendicular to the arrangement direction of the objective optical system 21 and the treatment tool channel 14. A prism 26 is disposed between the objective optical system 21 and the image sensor 20. Light shining on the prism 26 from the objective optical system 21 is reflected by a reflection surface 27 of the prism 26 and then shines on the photodetecting surface 20a of the image sensor 20.

As shown in FIG. 10, a total of four terminals, that is, a video terminal 23a, a control terminal 23b, a power terminal 23c, and a ground terminal 23d, are formed, as plural terminals 23, on the front surface (in which the photodetecting surface 20a is formed) of the image sensor 20 in a region that is outside a region that is opposed to the prism 26. The video terminal 23a, the control terminal 23b, the power terminal 23c, and the ground terminal 23d are arranged parallel with the arrangement direction of the objective optical system 21 and the treatment tool channel 14.

The video terminal 23a is most distant from the treatment tool channel 14. That is, the distance La of the video terminal 23a is the longest among the distances of the respective terminals 23a-23d from the center C of the treatment tool channel 14 defined in a plane that is perpendicular to the longitudinal axis A of the insertion unit 6. As a result, as in the example shown in FIG. 3, a phenomenon that noise that is radiated from a radio-frequency treatment tool inserted in the treatment tool channel 14 is mixed into a video signal that is output from the video terminal 23a can be suppressed, whereby a clear image that is necessary for proper observation and treatment can be obtained. The fact that the noise resistance of the endoscope 2 can be increased by the manner of disposition of the video terminal 23a rather than shielding contributes to narrowing of the insertion unit 6.

Although in the example of FIGS. 9 and 10 the ends the individual conductors of cables 24 are directly connected to the respective terminals 23, as in the example of FIG. 2 the ends of the individual conductors of the cables 24 may be connected to the terminals 23 via a flexible circuit board 25.

This specification discloses an endoscope comprising, in a tip portion of an insertion unit, an image sensor having plural terminals including a video terminal which outputs a video signal; and a tip potion of a treatment tool channel which extends in a longitudinal direction of the insertion unit, wherein a distance of the video terminal is the longest among distances of the respective terminals from a center of the treatment tool channel in a plane that is perpendicular to the longitudinal axis.

The disclosed endoscope may be such that the plural terminals include a power terminal which is supplied with operation power of the image sensor, and the distance of the power terminal is the shortest.

The disclosed endoscope may be such that the plural terminals include a ground terminal and the distance of the ground terminal is the shortest.

The disclosed endoscope may be such that the plural terminals are provided on a back surface that is opposite to a photodetecting surface of the image sensor.

The disclosed endoscope may be such that the number of plural terminals is equal to four.

The disclosed endoscope may be such that the plural terminals are arranged in a matrix of two rows and two columns each of which is parallel with a corresponding one of four sides of the back surface.

Although the invention has been described above in relation to preferred embodiments and modifications thereof, it will be understood by those skilled in the art that other variations and modifications can be effected in these preferred embodiments without departing from the scope and spirit of the invention.

What is claimed is:

1. An endoscope comprising, in a tip portion of an insertion unit of the endoscope:
    an image sensor having plural terminals including a video terminal which outputs a video signal; and
    a tip portion of a treatment tool channel which extends in a longitudinal axis of the insertion unit, wherein:
    a distance of the video terminal is longest among distances of the plural terminals from a center of the treatment tool channel in a plane that is perpendicular to the longitudinal axis,
    wherein the plural terminals comprise a ground terminal, and the distance from the ground terminal to the center of the treatment tool channel is the shortest of the distances from the plural terminals to the center of the treatment tool channel.

2. The endoscope according to claim 1, wherein the plural terminals are provided on a back surface of the image sensor that is opposite to a photodetecting surface of the image sensor.

3. The endoscope according to claim 2, wherein number of the plural terminals is four.

4. The endoscope according to claim 3, wherein the plural terminals are arranged in a matrix of two rows and two columns each of which is parallel with a corresponding one of four sides of the back surface.

* * * * *